US011624728B2

(12) United States Patent
Danilov et al.

(10) Patent No.: US 11,624,728 B2
(45) Date of Patent: Apr. 11, 2023

(54) METHOD FOR DETERMINING THE GEOMETRY OF A DEFECT AND FOR DETERMINING A LOAD LIMIT

(71) Applicant: Rosen Swiss AG, Stans (CH)

(72) Inventors: Andrey Danilov, Lingen (DE); Johannes Palmer, Lingen (DE)

(73) Assignee: Rosen Swiss AG, Stans (CH)

( * ) Notice: Subject to any disclaimer, the term of this patent is extended or adjusted under 35 U.S.C. 154(b) by 0 days.

(21) Appl. No.: 16/753,919

(22) PCT Filed: Sep. 28, 2018

(86) PCT No.: PCT/EP2018/076514
§ 371 (c)(1),
(2) Date: Jul. 15, 2020

(87) PCT Pub. No.: WO2019/068588
PCT Pub. Date: Apr. 11, 2019

(65) Prior Publication Data
US 2020/0340948 A1 Oct. 29, 2020

(30) Foreign Application Priority Data
Oct. 6, 2017 (EP) .................................... 17195267

(51) Int. Cl.
*G01N 27/83* (2006.01)
*G01N 33/2045* (2019.01)
(52) U.S. Cl.
CPC ......... *G01N 27/83* (2013.01); *G01N 33/2045* (2019.01)

(58) Field of Classification Search
CPC ........................... G01N 27/83; G01N 33/2045
See application file for complete search history.

(56) References Cited

U.S. PATENT DOCUMENTS

| 6,316,937 | B1 * | 11/2001 | Edens | G01N 27/82 |
| | | | | 324/229 |
| 7,013,224 | B2 * | 3/2006 | Landry | G21C 17/003 |
| | | | | 702/33 |
| 8,190,378 | B2 * | 5/2012 | Sakai | G01N 3/32 |
| | | | | 702/33 |
| 8,494,827 | B2 * | 7/2013 | Mutlu | G06F 30/23 |
| | | | | 703/10 |

(Continued)

OTHER PUBLICATIONS

International Search Report dated Dec. 7, 2018 (PCT/EP2018/076514).

(Continued)

*Primary Examiner* — Stephanie E Bloss
(74) *Attorney, Agent, or Firm* — Alix, Yale & Ristas, LLP

(57) ABSTRACT

Method for determining the geometry of multiple defects in a magnetizable object using a reference data record of the object, comprising determining an initial defect geometry as starting defect geometry, determining a first MFL prediction data record as starting prediction data record on the basis of the starting defect geometry, and iteratively adapting the starting defect geometry to the geometry of the real defect(s) by means of the EDP unit and by means of multiple expert routines (11) running in competition and preferably in parallel with one another.

20 Claims, 6 Drawing Sheets

(56) References Cited

U.S. PATENT DOCUMENTS

| | | | |
|---|---|---|---|
| 2013/0090902 A1* | 4/2013 | Yao | E21B 43/26 |
| | | | 703/2 |
| 2015/0213166 A1* | 7/2015 | Mills | G06F 30/23 |
| | | | 703/2 |
| 2016/0178580 A1* | 6/2016 | Huang | G01N 27/83 |
| | | | 702/189 |
| 2016/0187523 A1* | 6/2016 | Sanmartin | G01N 27/82 |
| | | | 324/339 |
| 2016/0245779 A1 | 8/2016 | Khalaj Amineh et al. | |
| 2016/0252481 A1* | 9/2016 | Zheng | G01M 3/40 |
| | | | 324/238 |
| 2017/0176629 A1* | 6/2017 | Omeragic | G01V 3/28 |
| 2017/0372196 A1* | 12/2017 | Traidia | G06N 3/08 |

OTHER PUBLICATIONS

European Communication under Article 94(3) EPC for Application No. 18 782 929.6-1020 dated Aug. 5, 2021; 6 pgs.
"Concurrent, Parallel and Distributed Systems"; Computer Science, https://computingstudy.wordpress.com/concurrent-parallel-and-distributed-systems/; 5 pgs.

* cited by examiner

METHOD FOR DETERMINING THE GEOMETRY OF A DEFECT AND FOR DETERMINING A LOAD LIMIT

BACKGROUND

The present invention relates to a method for determining the geometry of a defect and to a method for determining a load limit for an object that is subject to pressure loading at least during operation.

One of the fundamental purposes of pipeline inspections, in particular using what are known as intelligent pigs, is the prediction of safe operating conditions, which arise from the state of the pipeline. In particular, pipeline operators are interested in the state of any welds and in the number and size of defects. Defects are for example regions with metal losses on account of corrosion, cracks or other weakenings in a wall of an object intended in particular for supplying or transporting liquid or gaseous media. These include pipes, pipelines or tanks, for example.

Knowledge of the maximum pressure ("maximum burst pressure") for a pipeline, beyond which the pipeline is destroyed, is relevant to the operating pressures producible in the pipeline. Accordingly, accurate prediction of this pressure is important. At present, calculation of this limit value involves a defect merely being approximated in terms of its length, width and depth and therefore being considered as a box. Specifically for metal losses on account of corrosion on the outside or inside of a pipeline, this necessary conservative approach is disadvantageous, however, because the simplified geometric figures necessarily overestimate the present structure of the defect. This results in underestimation of the maximum burst pressure of the object and hence in underestimation of the permitted operating pressures. An object operable at higher pressure such as a pipeline or a gas tank can be operated much more economically, however.

It is prior art to measure corrosion of an object by having scans of magnetic flux leakage data (MFL data) on the basis of magnetic flux leakage measurements (MFL measurements) evaluated by specially trained persons to determine the size of the (corrosion) defects. The signals displayed in the scans are parameterized and evaluated in boxes. The assumptions required for this rating of the measurement results, which is also called sizing, are, firstly, proprietary. Secondly, the interpretation of the measurement results is greatly influenced by the empirical values of the evaluating persons. Ultimately, the quality of the predictions can only be ensured on the basis of examinations of the pipeline in situ. This in turn entails high costs for the operators. The most widely used industrial standard API 1163 describes the disadvantageous effects of this simplified approach. It is well documented that the quality of this approach is highly dependent on the knowledge of the examining persons. The approaches taken in practice are always an interpretation of the data obtained from an MFL measurement cycle, which interpretation is influenced by subjective factors.

Furthermore, approaches are known from scientific, i.e. theoretical, examination that involve successive variation and iterative methods of an assumed defect geometry being supposed to achieve the most accurate possible simulation of the measured signals by means of forward models. This involves the use of neural networks, for example. Theoretically, these approaches can provide solutions in the spirit of a resultant defect geometry, but these solutions are not necessarily realistic. This applies in particular to complex data records, which, among certain inverse problems, lead to unexpected, exotic and incorrect solutions. Whereas, in precisely defined and delimited test scenarios, scientific models of this kind yield a solution to the described problem in the form of defect geometries, this has not yet been successful to date for real measurement data, which have a multiplicity of interfering influences.

SUMMARY

It is therefore an object of the present invention to demonstrate a robust method for accurately reconstructing a real defect from the MFL measurement data record thereof and to perform the most accurate possible calculation of the load limit for an object affected by corrosion.

The object is achieved by a method according to claim 1 and, in respect of the determination of a load limit, by a method according to claim 15. Advantageous refinements of the invention can be found in the subclaims that refer back to these claims and in the description below.

According to the invention, there is provision for the determination of the geometry of one or more defects to be performed by means of a plurality of expert routines that are in competition with one another using in each case at least one dedicated search strategy or at least one dedicated algorithm, in particular in parallel on one electronic data processing (EDP) unit.

Such a method according to the invention for determining the geometry of one or more real, examined defects in a magnetizable object, in particular a pipe or a tank, using a reference data record of the object, which is produced on the basis of one or more MFL measurements, preferably comprises at least partially representing the object by means of an EDP unit, in particular on or by means of an at least three-dimensional object grid, and further comprises determining, in particular producing, an initial defect geometry as starting defect geometry, in particular on the object grid or on an at least two-dimensional defect grid, determining, in particular producing, a first MFL prediction data record as starting prediction data record on the basis of the starting defect geometry, in particular by simulating an MFL measurement or assigning an MFL data record, and iteratively adapting the starting defect geometry to the geometry of the real defect or defects by means of the EDP unit, this adapting being effected by means of multiple expert routines running in competition with one another and preferably in parallel with one another, wherein a respective expert defect geometry is produced in respective expert routines by means of at least one dedicated algorithm or a dedicated search strategy and on the basis of the starting defect geometry.

The expert routine has a dedicated algorithm when at least one of the algorithms available to the expert routine for adapting the defect geometry differs, at least in part, from the algorithms of a further expert routine. Preferably, stochastic processes can be used to distinguish between the algorithms of different expert routines. Each expert routine has at least one algorithm for adapting the defect geometry; preferably at least one expert routine has multiple algorithms available. Similarly, within an expert routine, the selection of an algorithm can be made or prescribed on the basis of stochastic processes.

According to the invention, there is furthermore provision for a respective expert prediction data record to be determined on the basis of the respective expert defect geometry, in particular by simulating an MFL measurement or assigning an MFL data record, wherein the expert defect geometry on which the respective expert prediction data record is based is then made available to at least one, preferably multiple, in particular all of the expert routines as a new starting defect geometry for further adapting to the geometry of the real defect or the real defects if the expert prediction data record is more similar to the reference data record than the starting prediction data record. Subsequently, i.e. for the next comparisons of the respective expert defect geometries with the new starting defect geometry, the expert prediction data record associated with the new starting defect geometry is used as new starting prediction data record. A measure of the similarity can be formed using a fitness function. The iterative adapting by means of the expert routines takes place until a stop criterion is met. The expert prediction data record and the first MFL prediction data record both show MFL fields associated with the respective assumed defect geometry. These can be calculated or simulated.

The expert prediction data record can be determined within the workflow of the expert routine and/or by means of a program module actuated separately from a monitoring routine.

The determination of the expert prediction data record on the basis of the respective expert defect geometry is furthermore effected in particular if sufficiently large databases containing calculated or measured MFL data pertaining to respective defect geometries are not yet available, by simulating an MFL measurement, which will be described below. Alternatively, the expert defect geometry can also be provided with an MFL data record from a sufficiently extensive database. There is also the possibility of a combined approach in which initially a database is searched for already existing MFL data and only then is a simulation performed in the event of a search with a negative outcome. This can lead all in all to fast determination of the respective expert prediction data record.

The method according to the invention is performed completely and in particular in automated fashion on an EDP unit, which may consist of multiple computers. The associated computer program can be a single program, or it can be a program package comprising a plurality of program modules that run on different EDP systems or EDP subunits, for example in a manner distributed depending on resources, and can be stored on respective EDP media there. A computer has, in particular, the typical means of a data processing unit such as one or more processors, at least temporary memory (RAM), data communication means, display and/or input units. Whereas the reference data record can preferably be selected under user control, the defect geometry is determined automatically during the iterations. Preferably, before the actual iteration, it is also possible for program parameters for selecting the algorithms available to the expert routines, determining an initial defect geometry, determining the first prediction data record and/or an expert prediction data record, which each show MFL fields, to be stipulated. By way of example, it is thus possible to stipulate whether the determination of the starting prediction data record is supposed to be created by means of a simulation of an MFL measurement on the basis of a grid representing the object with the defect or is supposed to be loaded from a database by means of a regression. In particular, in the case of the simulation of an MFL field, the parameters required for the comparison with the reference data record such as e.g. direction of the magnetization, strength of the magnetization, distance of the sensor from the object surface and/or speed of the measuring apparatus can be stipulated.

The expert routines competing with one another for resources of the EDP unit, which use their own search strategies to each look for their own solutions for determining the geometry of the real defect, in particular avoid the problem that exists with the theoretical approaches from the prior art that isolated solutions are found. In comparison with manual evaluation of the data records, the solution found is not only much better but also more easily comprehensible and documentable. Singular solutions in which an algorithm of whatever type gets stuck and the defect geometry is nevertheless not realistically reproduced are avoided in this manner.

Simulation of the flux leakage data associated with a geometry will normally require a representation of the object on or by means of a three-dimensional grid. The representation thereon is produced at least in part by virtue of at least the portion of the object with the defect or the defects and preferably adjoining regions being represented by or on the object grid. Alternatively, the flux leakage data can also be determined by means of a database query, for example by means of a regression function.

Although the method according to the invention can be performed to determine one or more defects within a reference data record at the same time, reference is made only to one defect for the most part below for the sake of simplicity.

The defect geometry can be assigned as a value for the MFL simulation given a clever choice of the representation of the object, in particular by means of or on the at least three-dimensional object grid, the grid elements or grid points. Depending on the geometry of the respective grids, this can require interpolations or grid adaptations.

In particular, the defect geometries that are the basis for determining the associated (MFL, or expert) prediction data records are defined by defect depths, which represent the depth of a corrosion on an object surface, for example, on the grid nodes of a two-dimensional defect grid, however. The two-dimensional representation of the defects allows the expert routines to work much faster than if the adapting of the defect geometry is performed on a three-dimensional grid.

To simulate the MFL measurement of a new defect geometry, the in particular two-dimensional defect grid is preferably interpolated onto the grid points of the object grid, wherein the surface of the object to be represented is adapted to the defect depths of the defect geometry. The simulation is then calculated on the in particular three-dimensional object grid. Alternatively, the flux leakage simulation can likewise be performed on a two-dimensional grid or by means of a regression model that is based on a database containing MFL data records based on finite element method simulations and/or MFL measurements.

The initial defect geometry, which is obtained or prescribed using a lookup table, a database comparison or an in particular one-time execution of an expert routine, for example, is taken as a basis for determining a first MFL prediction data record as starting prediction data record, in particular by simulating an MFL measurement. The simulation of the MFL measurement is performed as forward calculation by means of a finite element model, for example. The simulation of the flux leakage measurement involves the parameters required therefor being stipulated in accordance with the real measurement. This relates in particular to the magnetization direction, the magnetization field strength and/or the distance of the sensors above the surface of the object. On the basis of the initial defect geometry, an output prediction data record is then obtained as a simulated flux leakage measurement. This data record could be compared with the reference data record of the object already, but this regularly does not result in meaningful solutions at the beginning of the iteration.

A separate routine for stipulating an initial defect geometry as starting defect geometry is not absolutely necessary, but decreases the computing time required in the subsequent program cycles. Alternatively, the initial defect geometry can already be the result of a pass of an expert routine. The initial defect geometry can, additionally alternatively, be prescribed, for example by a completely flat, as it were defect-free, geometry.

The initial defect geometry is taken into the iterative approximation process of the expert routines in competition with one another as starting defect geometry. The expert routines themselves are independent of one another as dedicated program modules without direct interaction with one another, for example, and can be equipped with resources, in particular with computing time, on the basis of a monitoring routine or a main module.

Starting from the expert defect geometry developed in a respective expert module, an expert prediction data record is in turn determined for in particular each of these geometries, in particular by simulating an MFL measurement. Therefore, an expert prediction data record is produced as a simulated MFL measurement for each expert defect geometry, which is, in particular, available as a 2D data record of depth values of the defect. The simulation of the MFL fields on the basis of the respective expert defect geometries is effected in accordance with the previously described calculation of the starting prediction data record. In particular, the calculations on the basis of the respective expert defect geometries are performed in parallel. This can be accompanied by the setup of a database in which the flux leakage fields associated with respective defects are stored with the aim of being able to save computing time later and for other similar data.

Before the expert prediction data record is produced, it can be advantageous to adapt, in particular partially refine, the underlying grid, in particular the defect grid, if need be also the object grid, to calculate the expert defect geometry. This can be done using mesh morphing techniques, in particular, which involve the object or defect grid being refined by means of grid point displacement and/or division in particular into regions having high gradients in order to allow more accurate determination of the geometry or, subsequently, more accurate simulation. In other regions with lower gradients, the grid can become coarser in order to save computing time. As such, the grid used is automatically adapted for an optimum evaluation of the defect geometry. At the same time, this achieves a significant reduction in the number of unknowns, which means that computing time is in turn saved.

If the result of the comparison between the reference data record and the expert prediction data record of one expert routine is that said expert prediction data record is closer to the reference data record than the prior starting prediction data record, then the associated expert defect geometry is made available as starting defect geometry for the other expert routines and for the applicable expert routine. Taking this solution as a starting point, the other expert routines can then start from this geometry in a subsequent iteration step, unless they have found a better solution still, for example during their own defect geometry determination that is still ongoing, said solution then being made available to other or all expert routines.

Among the expert routines in competition with one another, preferably those that, as described below, are more successful in approximating the real measurement data than other competing expert routines are preferred in respect of the available resources of the EDP unit. Resources of the EDP unit are in particular the CPU or GPU time and/or the or a prioritization in the memory allocation.

Advantageously, the expert routines run (on the EDP unit) in competition with one another such that the resources of the EDP unit, in particular in the form of computing time, are distributed to a respective expert routine on the basis of a success rate, for which in particular the number of starting defect geometries calculated by the expert routine and made available for one or more other expert routines is taken into consideration, and/or on the basis of a reduction in a fitness function, for which in particular the number of expert prediction data records produced for the reduction is taken into consideration. The contest by the expert routines arises in particular by virtue of the program portion in the form of a monitoring routine then assigning the respective expert routines increased resources in particular in the form of computing time, preferably CPU or GPU time, if they are more successful than other expert routines. An expert routine is successful if it has found a defect geometry provided with a for example simulated leakage field measurement more suited to the reference data record, which defect geometry is made available to the other expert routines.

This can result, for example, in individual, particularly successful expert routines obtaining more than 50% of the total available computing time, which significantly reduces the total duration of the method according to the invention. At the same time, the program can prescribe that no or individual expert routines do not drop below a specific percentage of computing time, in order to avoid the problem of singular and exotic defect geometries or results from the individual routines. As such, if a hitherto successful expert routine finds just a local and no global solution, it is possible to find an escape route from the blockage situation otherwise occurring in the prior art.

The adapting by means of the expert routines is effected until a stop criterion is satisfied. This is for example a residual difference for the measured and simulated measurement data. It can also be an external stop criterion, for example based on the available computing time, or an in particular prescribable number of iterations or an in particular prescribable or prescribed computing time or a computing time determined from the available computing time.

It has been found that the accuracy of the defect determination is qualitatively improved by the method according to the invention. A resultant calculation of the maximum load capacity shows that for example pipelines can be operated for much longer. The accuracy of the defect determination is much increased. Maximum operating pressures obtained from the simulated defect geometry using the method described above and below can be estimated as up to 50% higher, which significantly reduces servicing and maintenance costs for the operation of the pipeline and the operators thereof. For the first time, it is now possible to achieve appropriate determination of the ASME B31G-2012 level 2 approach ("river bottom profile") for the "remaining strength algorithm" for MFL data records too.

Preferably, the resources of the EDP unit, in particular in the form of CPU time, will be distributed to a respective expert routine on the basis of the number of starting defect geometries made available by this expert routine for all expert routines. These can be for example a number of slots for calculating the expert prediction data records in the form of simulated MFL data records, the number of processor cores processing the computing task in parallel, or the like. There can furthermore be provision, within the context of the computer program product performing the method according to the invention, for said computer program product to adapt itself to the resources in the form of processor cores, memory space, memory architecture, graphics cards, etc., that are present in the EDP units. The prioritization of particularly preferred expert routines and the algorithms thereof makes detection of the real defect geometries much faster.

In order to minimize the problem of singular, local solutions further still, there is in particular provision for the geometry of the defect or of the defects to be determined by additionally using a further reference data record that is linearly independent of the first reference data record. The data records are linearly independent if they have been produced by MFL measurements with mutually angled magnetizations of the object. The magnetizations are mutually angled if the respective mean induced magnetic field strengths in the examined region are not parallel or congruent. In particular, the angle is between 40° and 140°, preferably between 80° and 100°, and particularly preferably 90°. The starting defect geometry is taken as a basis for determining a further starting prediction data record, in particular producing it by means of a further MFL simulation that takes into consideration the linear independence, i.e. in particular the different magnetizations, and an expert defect geometry is used as starting defect geometry only when the associated expert prediction data records determined for both independent magnetizations are more similar to the respective reference data records than the starting prediction data records determined for the two magnetizations and/or a fitness function taking into consideration both expert prediction data records is improved. The parallel or mutually accompanying processing of the two linearly independent data records and the use of a starting defect geometry whose simulated measurement data need to be better overall in respect of a similarity or a fitness function reduce the risk of singularities further. At the same time, the quality of the starting prediction data records available for all expert routines is improved. The number of iterations can therefore be reduced further.

In particular, the first reference data record is produced by means of an MFL measurement with axial magnetization and the second reference data record is produced by means of an MFL measurement with magnetization in the circumferential direction of the pipe. The respective magnetizations of the pipe or else of an object here are at right angles to one another, so that it is possible to obtain from the magnetic flux leakage measurements a maximum information content that is available to the full extent as a result of the simultaneous consideration of the applicable reference data records and the simulated expert prediction data records during the calculation. The method steps described below proceed taking into consideration the above analogously to when using two reference data records produced on the basis of linearly independent magnetizations.

The use of starting and/or expert prediction data records on the basis of a forward model for simulating the MFL measurements in particular by means of a finite element model means that the MFL measurement simulations are performed quickly. The simulation of the flux leakage measurements on the basis of the expert defect geometries can be performed by means of a dedicated program module that is called by the individual expert routines separately, in particular under the control and/or monitoring of a monitoring routine. It is also possible for multiple modules to be involved that are made available to a respective expert routine in a manner distributed over individual computer units.

Advantageously, the initial defect geometry is produced by means of a lookup table, by one of the expert routines and/or by a machine learning algorithm, which, as described above, improves the total computing time, in particular if additionally a grid adaptation already takes place.

In particular, the refinement of the object grid and/or the defect grid can take place in the regions in which the depth of the simulated defect or defects exceeds a threshold value, this threshold value being able to be prescribable, so that only gradients above a specific magnitude result in a change in the grid. For such a refinement, it is, in particular, possible for the total number of gradients of a new expert defect geometry to be taken into consideration in order to achieve a balance between the adaptation of the respective grid, in particular the object grid, and the subsequent computing operations.

The refinement of the grid with the aim of decreasing computing time can take place either on the basis of an initial reference data record already or before the expert prediction data record is calculated. For this too, it is possible to provide for a separate program module or individual submodules of the respective expert routines.

In particular, the refinement of the object and/or defect grid particularly advantageously by means of grid point displacement and/or division reduces the required CPU time by significantly reducing the number of independent variables that need to be used in the forward algorithm to simulate the MFL measurement. A grid point displacement can furthermore be used for adapting object or defect grids.

Preferably, the measure of similarity used for the expert prediction and reference data records is a fitness function in order to bring about a comparison of the simulated and measured data records on the basis of standard routines and appropriately quickly, i.e. while saving computing time.

In particular, the starting defect geometry in the form of a two-dimensional data record or a pointer referring thereto is stored in a memory area of the EDP unit that is accessible to all expert routines. This memory area is in particular again under the control of a monitoring routine, so that prioritization of individual expert routines can also be performed in this regard.

Instead of using the starting defect geometry, which is stored in a central memory area accessible to all expert routines, for example, each time at the beginning of a new iteration, it is possible for at least one expert routine to adapt its own expert defect geometry at the beginning of a new iteration while dispensing with adopting the starting defect geometry. For this, an expert routine can have a function specification in which, by way of example, search strategies used in other expert routines can be taken as a basis for specifically selecting a contrary strategy. In such a case, the expert routines can influence one another indirectly. Such an approach can be advantageous in particular if it is found that a routine that has always been successful hitherto favours an unrealistic solution. This can be detected on the basis of inadmissible values for the depth of a defect, for example. If an expert routine that does not adopt the starting defect geometry does not deliver improved solutions, it is automatically down-prioritized, so that increasingly less computing time is made available to it.

The stop or else convergence criterion assumed can preferably be a change in the starting defect geometry, or, more generally, in the geometry of the defect grid and/or the object grid, that fails to materialize after a plurality of iterations and can be referred to as substantial. The solution found hitherto is then the best one. Preferably, the stop criterion is chosen such that the observed variations in the flux leakage simulation that would lead to refinement of the object or defect grid are substantially, e.g. by a factor of less than 10, in particular of 2, below the variations that result from the individual measurement dispersion, in particular the measurement error, and that are individually specified on the basis of what are known as "essential variables" of the API 1163 standard, for example. The effect achieved thereby is that the accuracy of the final model is in the region of the accuracy prescribed by the measurement itself. Accordingly, the stop criterion used is preferably a comparison of the variation of the expert prediction data record with the measurement dispersion of the real data record. The stop criterion bringing about a program stop and in particular output or storage of the starting defect geometry calculated hitherto can preferably be specified by previously settable program parameters.

In particular, an expert routine has multiple algorithms available for adapting the expert defect geometry. These can involve approaches from the field of machine learning, stochastic optimization, empirical and/or numerical model functions. In particular, empirical values of evaluating persons can also be used in the expert routines. Preferably, the different algorithms are selected in an expert routine either on the basis of random number generation or by means of a selection function. This produces a sufficiently diverse approach that can be used to take into consideration all solutions in a targeted manner and under competitive conditions.

The object presented at the outset is also achieved by a method for determining a load limit for an object that is subject to pressure loading at least during operation and, in particular, is in the form of an oil, gas or water pipeline, wherein the method involves a data record that describes one or more defect(s) being used as input data record in a calculation of the load limit that is in particular in the form of forward modelling, wherein the input data record is initially produced using a method for determining the geometry of a defect as described above or below. The advantageous representation of the defect geometry, in particular as an unparameterized genuine three-dimensional geometry or as a two-dimensional surface area with respective depth values, renders simplifications hitherto assumed to be necessary in industry superfluous, which means that an increase in the accuracy of the defect determination as a whole is ensured in a hitherto unachievable manner for this reason too.

If the accuracy was previously restricted to the indication of the point of maximum depth of the defect, the entire profile is now ascertained with high accuracy. Typically, the accuracy of the maximum depth is increased to the extent achievable on the basis of the measurement accuracy, that is to say approximately ±5% of the wall thickness in comparison with approximately ±10% of the wall thickness previously in the case of the sizing based on the prior art described at the outset. However, the prediction of the load limit on the basis of the geometry of the defect, specifically for critical cases, achieves increases in accuracy of from for example ±50% hitherto to ±5% now. The advantage according to the invention is therefore in particular appropriate representation, achieved for the first time, of the defect geometry, which allows this very increase for the first time.

BRIEF DESCRIPTION OF THE DRAWINGS

Further advantages and details of the invention can be taken from the description of the figures below, in which, schematically.

DETAILED DESCRIPTION

Individual features of the exemplary embodiments described below can, in combination with the features of the independent claims, also result in developments according to the invention.

Figure 1:
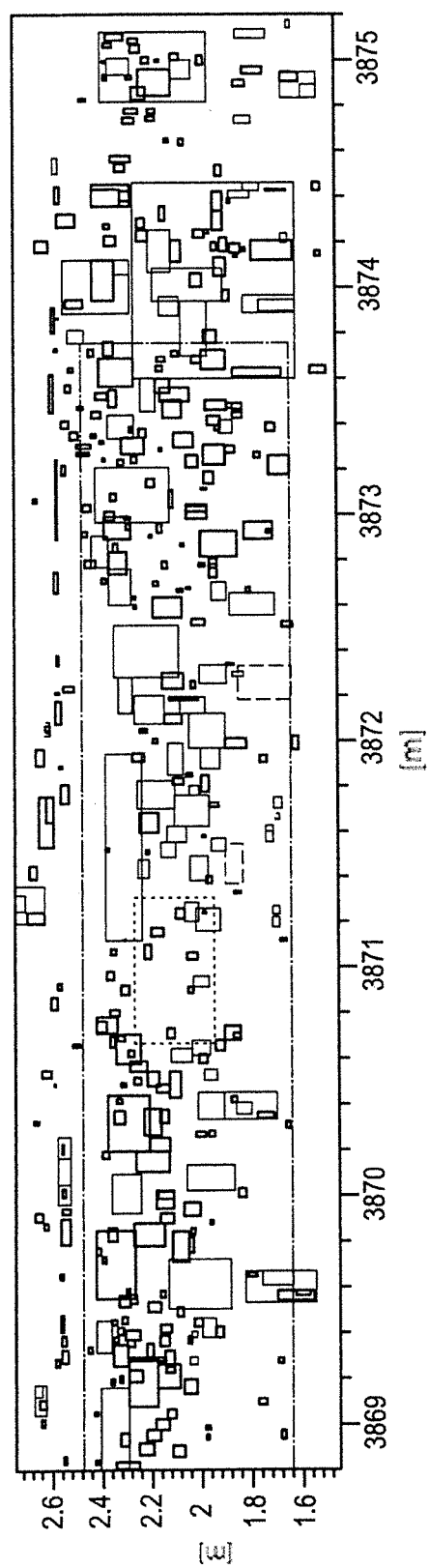
FIG. 1 shows a defect determination based on the prior art.

The prior art involves the evaluation of MFL data of a pipe as shown in FIG. 1 being performed by means of the in particular also empirically based definition of boxes. The boxes depicted in the figure have respective length, width and depth dimensions. The x and y axes are represented in metre units ([m]). A check on the actual defect geometry on which this evaluation is based by means of laser scanning, i.e. by means of a direct measurement, revealed that the maximum burst pressure determinable on the basis of the defect geometry assumed as a result of the MFL data evaluation is, at 4744.69 kPa, only 55.2% of the maximum burst pressure calculated on the basis of the actual geometry. From the prior art, the operating pressure for safe operation of the pipeline, which is revealed as 3621.29 kPa on the basis of the empirically-based evaluation, is distinctly below a possible safe operating pressure.

Figure 5:
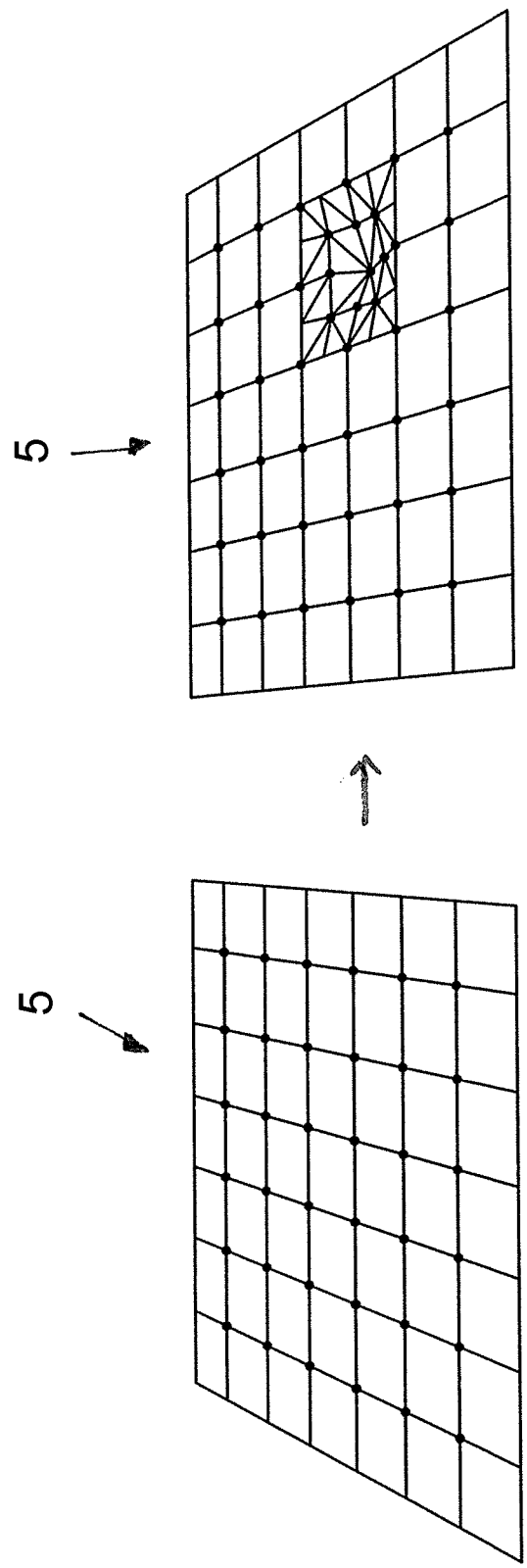
FIG. 5 shows a schematic depiction of a grid refinement as part of a method according to the invention.

In the method according to the invention, one exemplary embodiment involves the surface of a pipe being represented by a 2D mesh surface. The defect geometry can be described as a vector of depth values D located on a defect grid 5 (FIG. 5). This defect geometry is compared with the starting defect geometry on the basis of a result of a fitness function F(D) that takes into consideration the MFL fields associated with the respective geometries. In so doing, it is assumed that the lower the value of a fitness function, the closer the assumed expert defect geometry to the real geometry:

$$F(D) = \sum_M \|H_{cal}(D) - H_m\| + R(D)$$

Here, M is the number of data records that can be handled at the same time (real MFL data records), $H_{cal}$ is the result of a simulation of the MFL measurement, $H_m$ are the measured data from the MFL measurement (reference data record) and R (D) is a regularization term, which can be estimated as follows:

$$R(D) = \alpha |\nabla D|,$$

where α is a scaling term.

Figure 2:
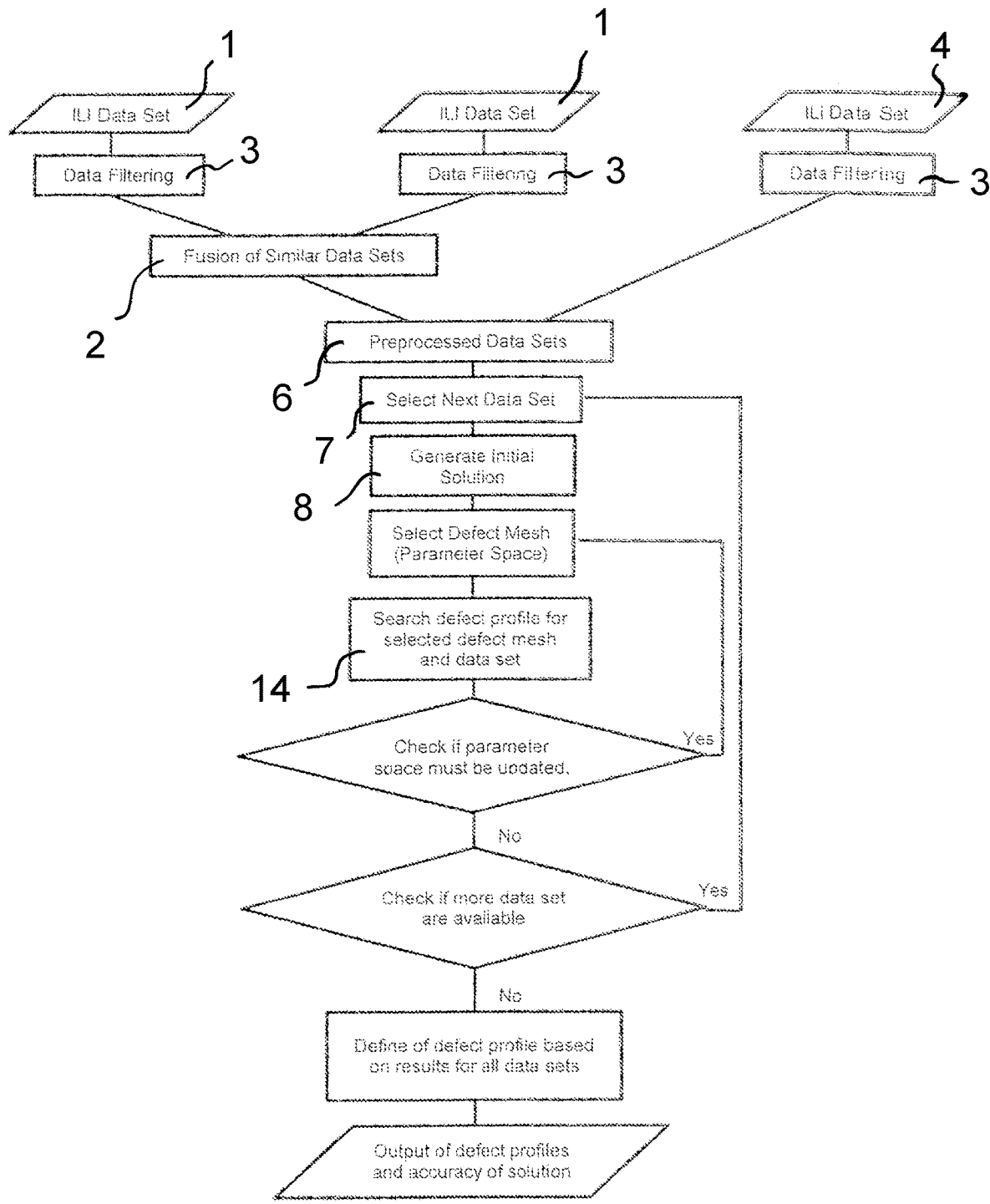
FIG. 2 shows a schematic depiction of a method according to the invention.

At least sections of the method sequence according to the invention are described below in accordance with FIG. 2, a plurality of the expert routines 11 that are in parallel and in competition being described just with one block 14.

By way of example, multiple passes by the same MFL pipeline pig can be combined as input data records as per box 2. Both data records 1 can be filtered and aligned with one another beforehand to improve combination (method step 3), for example in order to reduce any artefacts or background noise. Furthermore, a further data record 4, produced on the basis of a linearly independent, further magnetization and likewise filtered for the purpose of alignment with identical grid structures, can be used, so that, as per method section 6, two aligned reference data records obtained on the basis of measurement passes provided with linearly independent magnetizations are available.

Exactly aligned data records can be handled jointly, the method according to the invention implementing the simultaneous handling of the data records by using a fitness function that takes into consideration the combined data records.

In step 7, a first of the reference data records available in step 6 is selected for further handling. In addition to this, step 8 first of all involves an initial defect geometry being assumed, in particular generated in the present case, as starting defect geometry, said starting defect geometry being based for example on a normalized measurement signal $S(x,y)/(\max S)$. By way of example, the defect geometry can be derived from a threshold value function that takes into consideration the amplitude at grid points at which the signal is greater than a specific limit value/(e.g. 0.2):

$$G(x, y) = \begin{cases} 0, \text{ if } \frac{S(x, y)}{\max S} < l \\ \frac{S(x, y)}{\max S}, \text{ else} \end{cases}$$

The above approximation leads to a number of N defect depth values at the respective grid points:

$$D_i = i \text{ wt}/N^*G,$$

with wt as the thickness of the wall of the pipe. i is the index also used as a value for determining the defect depth value. For a defect geometry of this kind, the fitness function is calculated and the profile having the lowest function value is used as initial solution:

$$D_{ini} = \arg \min F(D_i)$$

This initial solution is then made available as starting defect geometry for the individual expert modules. To begin with, the number of parameter values (elements of the vector D) that describe the defect geometry can be kept as low as possible with the aim of reducing computing time. This is achieved by means of a dynamic grid adaptation, in particular. Since the number of depth values corresponds to the number of nodes in the defect grid 5, the number of nodes is at the same time also the number of defect parameters. Beginning with a comparatively coarse grid, it is progressively refined in relevant regions.

By way of example, given a prescribed node spacing of 14 mm, for example, an accompanying grid cell size of 14 mm×14 mm and defect limit values of 30%, 50% and 80% of the wall thickness, it is possible to achieve the refinement depicted in FIG. 5 in the relevant grid region, those cells that exceed the depth values above being progressively divided. The grid deformation then correlates with the assumed defect geometry, i.e. there is a larger number of grid points in regions having high gradients.

Figure 3:
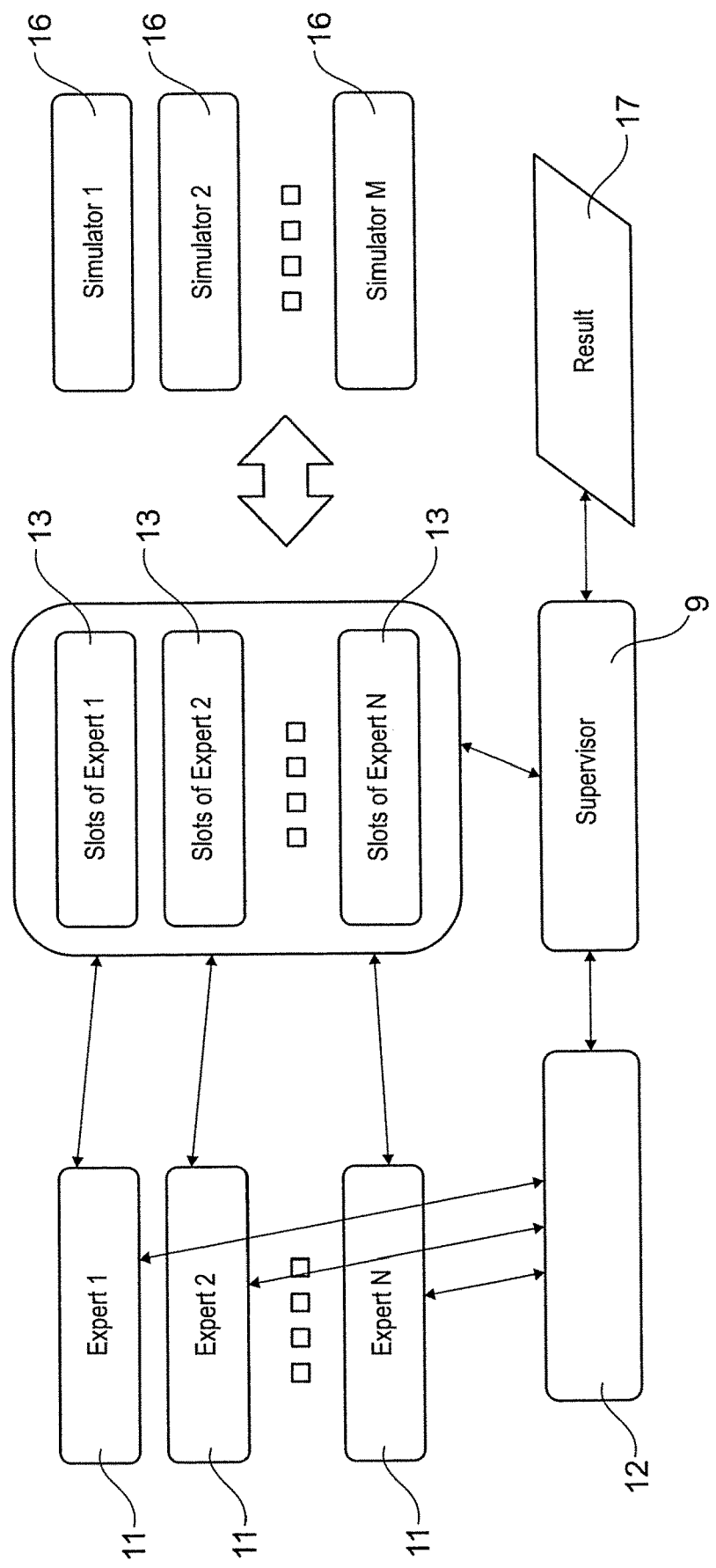
FIG. 3 shows a more detailed explanation of a portion of FIG. 2.

The EDP unit is used to simulate the sequence of the workflow of a group of expert routines 11 that are in competition with one another using the method according to the invention. To this end, the program can have various modules that, independently of one another and in particular not in sync with one another, can put data into specific areas of the EDP unit so that said data are processed further therein. This takes place in particular under the supervision of a monitoring routine 9 (FIG. 3a). A plurality of expert routines 11 therefore take the success defined above, i.e. for example the number of starting defect geometries written to a common memory area 12, as a basis for keeping a number of computing slots 13 in order to produce respective expert defect geometries and/or to be able to perform associated MFL simulations or to have them performed in the case of an independent MFL simulation module. This corresponds to block 14 according to FIG. 2, said block serving as an example of multiple expert routines 11 (FIG. 3a). On the basis of the individual computing slots 13, the present exemplary embodiment involves the MFL simulations of the individual expert defect geometries likewise being performed under the supervision of the monitoring routine 9 in the simulation modules 16 for the purpose of creating the expert prediction data records. The more slots 13 are available for an expert routine, the greater the proportion of EDP resources for this expert routine. Preferably, the number of program modules required for performing MFL simulations is equal to the number of slots. The monitoring routine 9 monitors the number of iterations and the resultant changes in the starting defect geometry and, furthermore, monitors whether an associated stop criterion is reached. Subsequently, the result is output in accordance with block 17.

The number of computing slots 13 available for an expert routine 11 and the subsequently available simulation routines can vary such that a first expert routine can utilize up to 50%, for example, of the total computing time available for the computing slots and simulation routines.

The memory area 12 is used to store the starting defect geometries as depicted. It can be a memory area accessible to the expert routines 11. It can likewise be used to store log files of the expert routines 11 and monitoring routine 9 and also instructions to the expert routines 11 that are then implemented by them independently. By way of example, these can be an interrupt command that is applied when the stop criterion is reached.

Preferably, the expert routines 11 are independent program modules that produce new expert defect geometries and put them into the simulation routines 16. Furthermore, the fitness function described at the outset can be produced in the expert routines 11 on the basis of the expert prediction data record and can be compared with the starting prediction data record stored in the area 12. If the expert prediction data record is more similar overall to the reference data record, or, in the case of linearly independent measurement data records, then accordingly to the two reference data records, than the data record stored in the area 12, this expert prediction data record is then used as new starting prediction data record.

By way of example, a new defect geometry is produced in the expert routines 11 on a random number basis. This can be accomplished by using machine learning algorithms or empirical rules. Advantageously, however, additionally improved convergence of the solutions is accomplished by providing for the implementation of at least two base expert routines as described below.

These search strategies, which are preferably always implemented for a method according to the invention, are based on an assumed probability distribution $p(x,y)$ of grid points, the depth value of which results in a maximum reduction in the fitness function. The probability function is used to identify N grid points $(x_n, y_n)$. At each of the points considered, the depth function, which describes the depth of the corrosion at the grid location, for example, is changed by ΔD, the arithmetic sign of the change being distributed on the basis of random number generation. The number of selected points N can also be chosen on a random number basis:

$$D_{new}(x, y) = \begin{cases} D(x_n, y_n) \mp \Delta D, \text{ for selected points} \\ D(x, y), \text{ else} \end{cases}$$

A selection of the probability function p (x,y) can be used to implement different expert strategies, for example:

$$p(x, y) = \frac{D(x, y)}{\|D(x, y)\|}$$

This algorithm produces a variation in the defect depths in which the grid points having the greatest depth are favoured. Another strategy can have the following appearance:

$$p(x, y) = \frac{H_{the\ best}(x, y) - H_m(x, y)}{\|H_{the\ best}(x, y) - H_m(x, y)\|}$$

Such an algorithm varies the defect geometry at positions at which the simulated measurement signal for the best known solution $H_{the\ best}$ has the greatest difference from the measured signal.

On that basis, variations in the number of grid points to be considered and in the ΔD allow different expert routines, or the algorithms thereof, to be set up. By way of example, the six expert routines below can be used:

1. $p(x, y) = \frac{D(x, y)}{\|D(x, y)\|}, N = 1$ and $\Delta D = 1\%$ wall thickness 2. $p(x, y) = \frac{D(x, y)}{\|D(x, y)\|}, N = 2$ and $\Delta D = 5\%$ wall thickness 3. $p(x, y) = \frac{D(x, y)}{\|D(x, y)\|}, N = 3$ and $\Delta D = 5\%$ wall thickness 4. $p(x, y) = \frac{H_{the\ best}(x, y) - H_m(x, y)}{\|H_{the\ best}(x, y) - H_m(x, y)\|},$
   $N = 1$ and $\Delta D = 1\%$ wall thickness 5. $p(x, y) = \frac{H_{the\ best}(x, y) - H_m(x, y)}{\|H_{the\ best}(x, y) - H_m(x, y)\|},$
   $N = 2$ and $\Delta D = 5\%$ wall thickness 6. $p(x, y) = \frac{H_{the\ best}(x, y) - H_m(x, y)}{\|H_{the\ best}(x, y) - H_m(x, y)\|},$
   $N = 3$ and $\Delta D = 5\%$ wall thickness The monitoring routine 9 depicted in FIG. 3a has two functions, in particular, as described: first, a check is performed to ascertain whether the stop criterion is reached and, second, the resources of the EDP unit are done between the individual experts on the basis of the successes thereof. A measure of the success is $$P = \frac{\Delta F}{N},$$

where ΔF is the reduction in the fitness function F owing to the result of the respective expert routine and N is the number of simulations necessary therefor. A rating of the n expert routines can be assumed to be $$R_n = \frac{P_n}{\sum P_i}.$$

The number of computing slots $N_S$ for an expert routine in one iteration is then $$N_S = \text{int}(R_n N_{all}),$$

where $N_{all}$ is the number of all available slots.

The simulation routines 16 are used to simulate an MFL measurement for an expert defect geometry. An expert routine can iterate until it finds a solution whose expert prediction data record is better than the starting prediction data record stored in the area 12. If this is the case, the expert routine 11 can process a further linearly independent data record or set out from the already improved solution to achieve further better solutions.

If multiple data records from different iterations that cannot be concordantly aligned were worked through by the expert routines, it is likewise possible for the performance of the method according the invention to involve the geometries obtained being overlaid in automated fashion, the maximum depth at the individual grid points being taken as a conservative estimate:

$$D(x, y) = \max_N D_n(x, y)$$

for n=1 . . . N, where N is the number of data records that need to be processed in succession. A resulting depth profile obtained over such an overlay of defect geometries can in turn be taken as a starting point for simulating an MFL signal. The error obtained can be obtained from the errors of the respective data records in the individual calculations:

$$E = \|H_{cal}(D) - H_m\|$$

In order to demonstrate the efficiency of the proposed method, a multiplicity of test scenarios were performed, the data of two MFL inspection passes performed using mutually linearly independent magnetizations being used below in accordance with FIG. 4.

Figure 4:
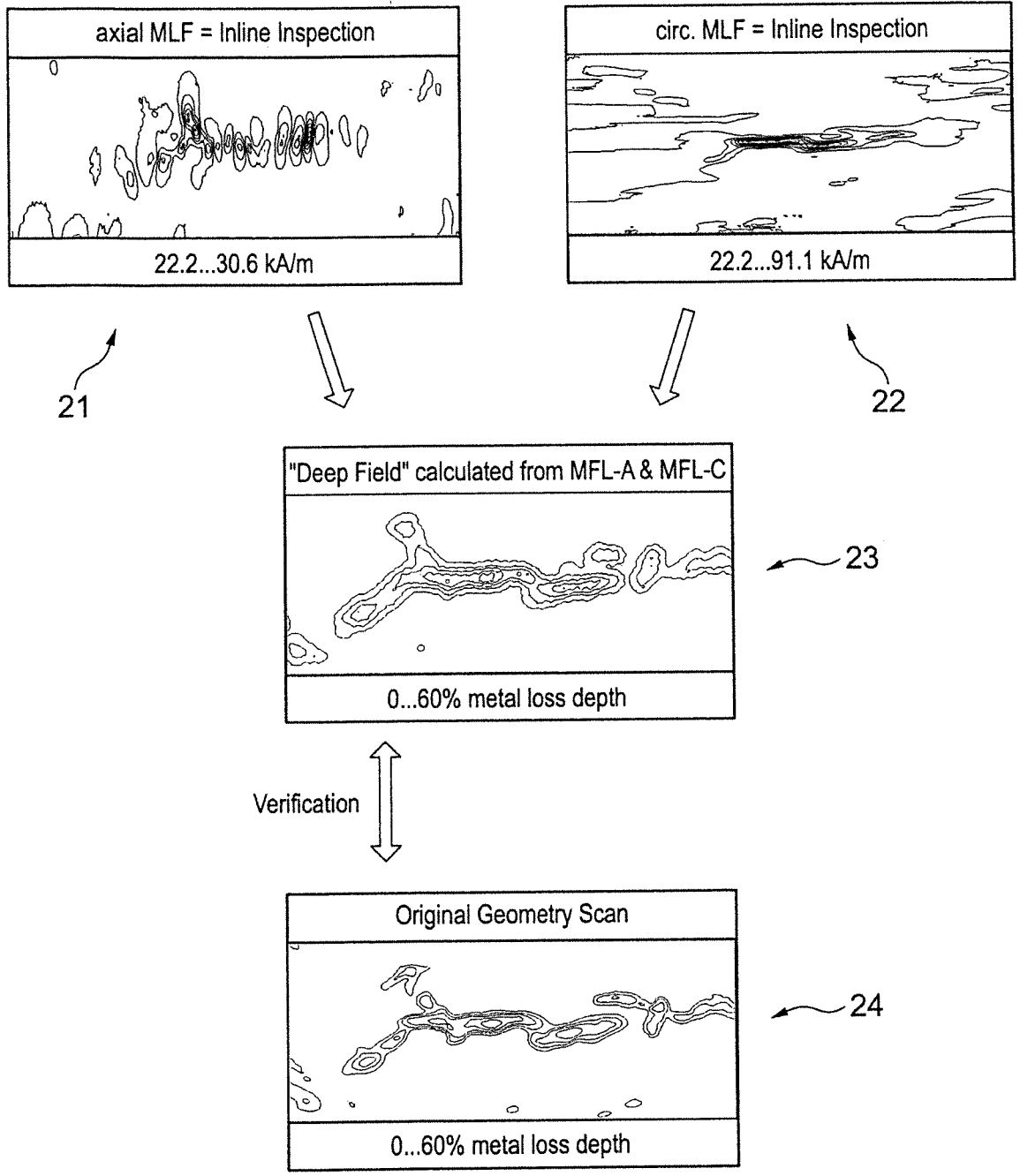
FIG. 4 shows comparison of a result of a method according to the invention with measurement data.

FIG. 4 shows a depiction, labelled No 21, of a real MFL measurement with magnetization running in the axial direction, while depiction 22 results from a measurement taken in the circumferential direction. The computation result for the defect geometry, which was obtained using the method according to the invention described above, is indexed by 23. The contour lines evenly split the region between 0 and 60% metal loss depth, as in depiction 24 too. Depiction 24 shows the actually scanned and hence directly measured exterior surface of the pipe section associated with depictions 21 and 22. A very high level of concordance between the laser scan measurement and the solution achieved by means of the method according the invention is obtained. This is much better than the solution based on the evaluation known in the prior art. In this case, it can be assumed that the discrepancies between the result based on the method according invention and that of the laser scan measurement are predominantly present on account of technical tolerances.

Figure 6:
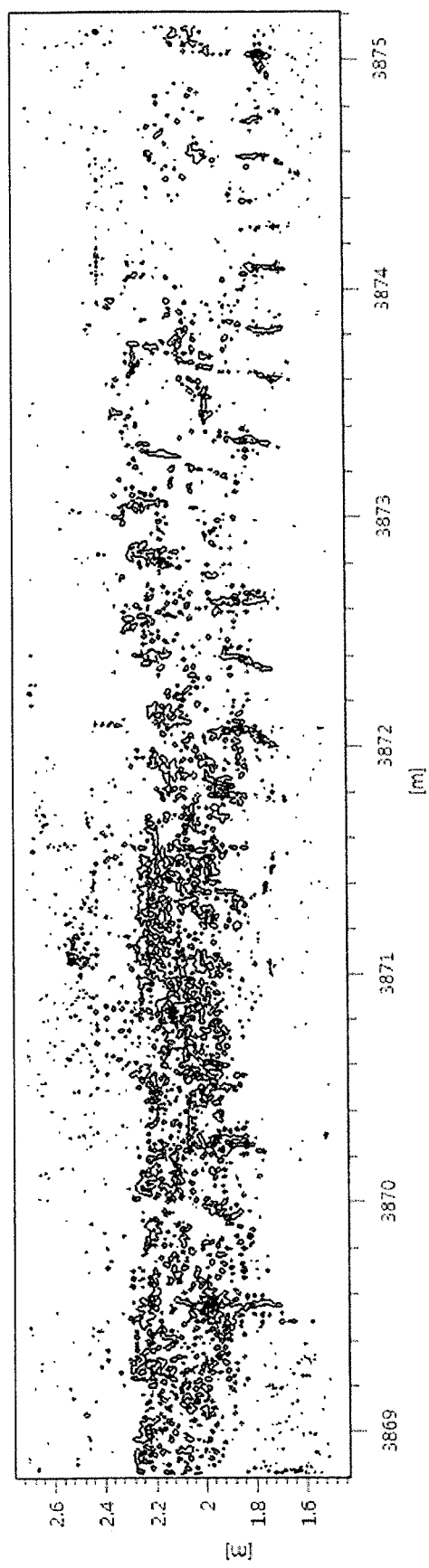
FIG. 6 shows a result of a method according to the invention.

Based on the conventional approach involving ascertainment of the defect geometry as established in the prior art and ultimately depicted in FIG. 1, the aforementioned maximum burst pressure of 4744.69 kPa is obtained. Based on the method according to the invention, the defect geometry shown in FIG. 6 (contour lines at 2 mm depth) and, based thereon, a maximum burst pressure of 8543.46 kPa are obtained for the MFL data record on which FIG. 1 is also based. In the present case, this comes to within 99.4% of the maximum burst pressure that was determined on the basis of the actual defect geometry ascertained by laser scan. Accordingly, a pipeline examined using the method according to the invention can be operated at a safe operating pressure of 6520.53 kPa. This results in significant advantages for pipeline operators in comparison with the safe operating pressure of 3621.29 kPa based on the evaluation according to the prior art (FIG. 1). The method according to the invention allows the state of a pipe and hence the pressure specifiable for safe operation of the pipeline to be specified much more realistically, while safety of operation continues to be ensured. The method according to the invention with the expert routines competing for resources of the EDP unit allows such a result to be made available to the operators of pipelines more quickly than or at least in the same evaluation time as in the prior art.

The invention claimed is:

1. A method for determining a geometry of a real, examined defect in a magnetizable object in the form of a pipeline or tank for oil, gas or water that is subject to pressure loading during operation so as to accurately predict a maximum burst pressure of the magnetizable object, said method comprising the following steps executed in an electronic data processing (EDP) unit having resources in the form of CPU time, GPU time, or memory allocation, said method comprising:

receiving a reference data record of the magnetizable object produced by at least one magnetic flux leakage (MFL) measurement of a region of the magnetizable object including the real, examined defect;

at least partially representing the region of the magnetizable object on a three-dimensional object grid or two-dimensional defect grid;

determining an initial defect geometry as a starting defect geometry on the object grid or defect grid;

determining a first MFL prediction data record as a starting prediction data record on the basis of the starting defect geometry by simulating an MFL measurement of the starting defect geometry or assigning an MFL data record corresponding to the starting defect geometry;

iteratively adapting the starting defect geometry to the geometry of the real, examined defect by running multiple expert routines in competition with one another, each of said expert routines executing at least one algorithm for adapting the starting defect geometry that differs from algorithms of the other expert routines, each of said expert routines producing an expert defect geometry that differs from the starting defect geometry;

for at least one expert defect geometry produced, determining an expert prediction data record by simulating an MFL measurement of the expert defect geometry or assigning an MFL data record corresponding to the expert defect geometry;

comparing the expert prediction data record to the reference data record and the starting prediction data record;

making the expert defect geometry produced by one of the expert routines available to a plurality of the expert routines as a new starting defect geometry for further iterative adaptation if the expert prediction data record produced by said one of the expert routines is more similar to the reference data record than the starting prediction data record; and using the expert prediction data record associated with the new starting defect geometry as a new starting prediction data record for said step of comparing, distributing the resources of the EDP to the expert routines based on the number of new starting defect geometries produced by each of the multiple expert routines, or on the basis of a reduction in a fitness function for which the number of expert prediction data records produced for the reduction by each of the expert routines is taken into consideration;

repeating said steps of iteratively adapting and comparing until a stop criterion is met; and after the stop criterion is met, producing a data record from the new starting defect geometry useable in a calculation of the load limit.

2. The method of claim 1, wherein the fitness function is used as a measure of the similarity of the expert prediction data record and the reference data record.

3. The method of claim 1, comprising receiving a second reference data record that is linearly independent of the reference data record, said second reference data record produced by a second MFL measurement of the region, the starting defect geometry is used as a basis for determining a second starting prediction data record by an MFL simulation that takes into consideration the linear independence, and an expert defect geometry is used as a new starting defect geometry only when the expert prediction data record determined for the second reference data record is also more similar to the second reference data record than the second starting prediction data record, or a fitness function taking into consideration the expert prediction data record and the second expert prediction data record is improved.

4. The method of claim 3, wherein the reference data record was produced by an MFL measurement with a direction of magnetization perpendicular to a direction of magnetization used for the second MFL measurement.

5. The method of claim 1, wherein the starting prediction data record or the expert prediction data records are produced on the basis of a finite element model.

6. The method of claim 1, wherein the initial defect geometry is produced by reference to a look up table, by one of the expert routines, or by a machine learning algorithm.

7. The method of claim 1, wherein the defect grid or object grid is refined in regions where a depth of an expert defect geometry exceeds a threshold value.

8. The method of claim 1, wherein the defect grid or the object grid is refined before the expert prediction data record is determined.

9. The method of claim 1, wherein the starting defect geometry or a pointer referring thereto is stored in a memory area of the EDP unit that is accessible to the multiple expert routines.

10. The method of claim 1, wherein the stop criterion is a substantial change in the starting defect geometry, or in a geometry of the object grid, or in a geometry of the defect grid or a substantial change in the starting prediction data record or expert prediction data record, that fails to materialize after a plurality of iterations.

11. The method of claim 1, wherein the stop criterion is a comparison of a variation of the expert prediction data record with a measurement dispersion of the MFL measurements used to produce the reference data record.

12. The method of claim 1, wherein the at least one algorithm assigned to an expert routine comprises multiple algorithms for adapting the expert defect geometry comprising machine learning, stochastic optimization, empirical or numerical model functions.

13. The method of claim 12, wherein the at least one algorithm is selected or changed on the basis of random number generation or by means of a selection function.

14. The method of claim 1, comprising the step of:
using the data record produced from the new starting defect geometry to calculate a load limit of the magnetizable object.

15. The method of claim 3, comprising the step of:
using the data record produced from the new starting defect geometry to calculate a load limit of the magnetizable object.

16. The method of claim 1, wherein said plurality of expert routines comprises all of the expert routines.

17. A method for determining a geometry of a real, examined defect in a magnetizable object in the form of a pipeline or tank for oil, gas or water that is subject to pressure loading during operation in order to accurately calculate a load limit of the magnetizable object, said method comprising the following steps executed in an electronic data processing (EDP) unit having resources in the form of CPU time, GPU time, or memory allocation, said method comprising:
receiving a reference data record of the magnetizable object produced by at least one magnetic flux leakage (MFL) measurement;
at least partially representing the magnetizable object on a three-dimensional object grid or two-dimensional defect grid;
determining an initial defect geometry as a starting defect geometry on the object grid or defect grid;
determining a first MFL prediction data record as a starting prediction data record on the basis of the starting defect geometry by simulating an MFL measurement of the starting defect geometry or assigning an MFL data record corresponding to the starting defect geometry;
iteratively adapting the starting defect geometry by running multiple expert routines in competition with one another, each of said expert routines executing at least one algorithm for adapting the starting defect geometry that differs from algorithms of the other expert routines, each of said expert routines producing an expert defect geometry that differs from the starting defect geometry;
using the expert defect geometry to determine an expert prediction data record by simulating an MFL measurement of the expert defect geometry or assigning an MFL data record corresponding to the expert defect geometry;
comparing the expert prediction data record to the reference data record and the starting prediction data record;
making the expert defect geometry produced by one of the expert routines available to a plurality of the expert routines as a new starting defect geometry for further iterative adaptation if the expert prediction data record produced by said one of the expert routines is more similar to the reference data record than the starting prediction data record;
using the expert prediction data record associated with the new starting defect geometry as a new starting prediction data record for said step of comparing;
distributing the resources of the EDP to the expert routines based on the number of new starting defect geometries produced by each of the multiple expert routines;
continuing said iterative adapting and comparing until a stop criterion is met;
after the stop criterion is met, using the new starting defect geometry to calculate the load limit for the magnetizable object.

18. A method for determining a geometry of a real, examined defect in a magnetizable object in the form of a pipeline or tank for oil, gas or water that is subject to pressure loading during operation in order to accurately calculate a load limit of the magnetizable object, said method comprising the following steps executed in an electronic data processing (EDP) unit having resources in the form of CPU time, GPU time, or memory allocation, said method comprising:
receiving a first reference data record of the magnetizable object produced by a first magnetic flux leakage (MFL) measurement of a region of the magnetizable object including the real, examined defect;
receiving a second reference data record of the magnetizable object produced by a second MFL measurement of the region, said second reference data record being linearly independent of the first reference data record;
at least partially representing the region of the magnetizable object on a three-dimensional object grid or two-dimensional defect grid;
determining an initial defect geometry as a starting defect geometry on the object grid or defect grid;
for the first reference data record, determining a first MFL prediction data record as a first starting prediction data record on the basis of the starting defect geometry and parameters of the first MFL measurement;
for the second reference data record, determining a second MFL prediction data record as a second starting prediction data record on the basis of the starting defect geometry and parameters of the second MFL measurement;
iteratively adapting the starting defect geometry to the geometry of the real, examined defect by running multiple expert routines in competition with one another, each of said expert routines executing at least one algorithm for adapting the starting defect geometry that differs from algorithms of the other expert routines, each of said expert routines producing an expert defect geometry that differs from the starting defect geometry;
using the expert defect geometry to determine a first expert prediction data record by simulating an MFL measurement of the expert defect geometry or assigning an MFL data record corresponding to the expert defect geometry taking into account the parameters of the first MFL measurement;
using the expert defect geometry to determine a second expert prediction data record by simulating an MFL measurement of the expert defect geometry or assigning an MFL data record corresponding to the expert defect geometry taking into account the parameters of the second MFL measurement;
comparing the first expert prediction data record to the first reference data record and the first starting prediction data record;
comparing the second expert prediction data record to the second reference data record and the second starting prediction data record;

making the expert defect geometry produced by one of the multiple expert routines available as a new starting defect geometry for iterative adapting only when the first expert prediction data record is more similar to the first reference data record than the first starting prediction data record and the second expert prediction data record is more similar to the second reference data record than the second starting prediction data record;
distributing the resources of the EDP among the multiple expert routines based on the number of new starting defect geometries produced by each of the multiple expert routines, and
repeating said steps of iteratively adapting and comparing until a stop criterion is met; and
after the stop criterion is met, producing a data record from the new starting defect geometry useable in a calculation of the load limit.

19. The method of claim 18, comprising:
replacing the first expert prediction data record with the first expert prediction data record associated with the new starting defect geometry for said step of comparing; and
replacing the second expert prediction data record with the second expert prediction data record associated with the new starting defect geometry for said step of comparing.

20. The method of claim 18, comprising:
wherein making the expert defect geometry produced by one of the multiple expert routines available as a new starting defect geometry for iterative adapting comprises storing the new starting defect geometry or a pointer referring thereto in a memory area of the EDP unit that is accessible to the multiple expert routines.

* * * * *